United States Patent
Surburg et al.

(10) Patent No.: US 6,458,972 B1
(45) Date of Patent: Oct. 1, 2002

(54) PROCESS FOR THE PREPARATION OF MACROCYCLIC ESTERS

(75) Inventors: Horst Surburg, Holzminden; Dirk Müller; Stephan Klein, both of Gladbach; Christine Mendoza-Frohn, Erkrath; Georg Ronge, Düsseldorf; Kai Verkerk, Köln, all of (DE)

(73) Assignee: Haarmann & Reimer GmbH, Holzminden (DE)

( * ) Notice: Subject to any disclaimer, the term of this patent is extended or adjusted under 35 U.S.C. 154(b) by 0 days.

(21) Appl. No.: 09/934,383

(22) Filed: Aug. 21, 2001

(30) Foreign Application Priority Data

Aug. 23, 2000 (DE) .......................... 100 41 198

(51) Int. Cl.$^7$ .................. C07D 313/00; C07D 321/00; C07D 327/00
(52) U.S. Cl. .......................... 549/266; 549/10; 549/267
(58) Field of Search .......................... 549/10, 266, 267

(56) References Cited

U.S. PATENT DOCUMENTS

| 4,165,321 A | 8/1979 | Harris et al. ............. 260/340.2 |
|---|---|---|
| 4,187,222 A | 2/1980 | Bauer et al. ................ 260/343 |
| 4,594,434 A | 6/1986 | Cahill, Jr. et al. .......... 549/267 |
| 4,709,058 A | 11/1987 | Cahill, Jr. et al. .......... 549/267 |
| 4,803,288 A | 2/1989 | Kitamura et al. ........... 549/267 |
| 5,717,111 A | 2/1998 | Koehler et al. ............. 549/266 |
| 5,912,275 A | 6/1999 | Hall et al. .................... 521/48 |
| 6,034,052 A | 3/2000 | Körber et al. ................ 512/26 |

FOREIGN PATENT DOCUMENTS

JP    55-120581    9/1980

OTHER PUBLICATIONS

Houben–Weyl, Methoden der Organischen Chemie [Methods of Organic Chemistry] vol. 4/2 pp. 786–791, II Depolymerisationverfahren, a) Makrocyclische Säureanhydride.

*Primary Examiner*—Amelia Owens
(74) *Attorney, Agent, or Firm*—Joseph C. Gil; Noland J. Cheung

(57) ABSTRACT

Macrocyclic ester compounds can be prepared from oligoesters by thermal cleavage in the presence of a thermostable benzene derivative.

8 Claims, No Drawings

PROCESS FOR THE PREPARATION OF MACROCYCLIC ESTERS

FIELD OF THE INVENTION

The present invention relates to a process for the preparation of macrocyclic ester compounds from oligoesters by thermal cleavage in the presence of thermostable benzene derivatives. For the purposes of the present invention, thermostable refers to compounds which behave mostly inert during the oligoester cleavage at temperatures between 200° C. and 350° C.

BACKGROUND OF THE INVENTION

Musk fragrances are present in many perfume oils in not inconsiderable amounts. Accordingly, the annual worldwide requirement for musk fragrances is several thousand tons. By far the largest part is provided by the so-called polycyclic aromatic musk fragrances. It has become known that polycyclic aromatic musk fragrances can only be biodegraded with difficulty and consequently, being extremely lipophilic compounds, exhibit bioaccumulative behavior, i.e. they are able to accumulate in the fatty tissue of organisms. In the perfume industry, there is therefore, a pressing need for biodegradeable musk fragrances which are suitable both in terms of the odiferous properties and also in terms of price as replacements for the polycyclic aromatic compounds. In contrast to the polycyclic aromatic compounds, macrocyclic musk fragrances are regarded as biodegradeable (U.S. Pat. No. 6,034,052). The known processes cannot be carried out economically in a satisfactory manner.

It is known that macrocyclic ester compounds can be prepared by depolymerization of linear oligoesters of the corresponding aliphatic hydroxycarboxylic acids or dicarboxylic acids and alkylene glycols. The thermal depolymerization is usually carried out without a diluent under vacuum (<100 hPa) and at high temperatures (200–300° C.) in the presence of a catalyst. A codecisive factor for the cleavage yield achieved here is the molecular weight of the oligoester used. For this reason, control of this parameter during the oligoester formation is important. The condensation reaction must, accordingly, be terminated at almost complete conversions before the onset of the molar mass build-up typical of the polyester reaction. A measure which can be used here is, for example, the monitoring of the product viscosity. Alternatively, the condensation and thus, the oligoester formation can be carried out in the solvent chosen for the cleavage in order to avoid high molecular weights. EP A 0 260 680 has already indicated that it may be advantageous to control the molecular weight and the viscosity of the oligoesters used by targeted termination with monocarboxylic acids and/or monofunctional alcohols. Polyesters with acid and OH numbers below 20 or below 10, respectively, may be particularly advantageous.

During the depolymerization, the desired cyclization reaction is accompanied by a further polycondensation of the linear polyester and a further intermolecular crosslinking reaction. The yield of product decreases significantly as a result. Moreover, the crosslinking reactions lead to an increase in the viscosity and to adhesion of the product to the wall of the reactor. This favors the onset of decomposition reactions of the product; the decomposition products may considerably impair the odiferous properties.

These disadvantages in the case of depolymerization without a diluent can be overcome by carrying out the reaction in an inert reaction medium with a high boiling point. The choice of reaction medium here is decisive for the reaction yield which can be achieved and the quality of the product and thus also for the economic efficiency of the process. For example, EP A 0 260 680 has proposed olefin polymers, JP A 55-120 581 has proposed polyesters, polyether glycols, polyether glycol esters or only polyglycols, DE A 3225431 has proposed paraffins, and EP A 0 739 889 has proposed polyethylene glycol dialkyl ethers as high-boiling medium.

Although the use of these auxiliaries can increase the product yield relative to a cleavage without a diluent, said auxiliaries have the disadvantage that they mostly have a high melting point, which makes handling difficult. This disadvantage is all the more serious since one important requirement in the art is that the thermostable reaction medium which is left behind in the distillation still can be removed from the reactor easily when the reaction is interrupted or complete, which is virtually impossible in the case of the known processes with the traditional reaction media.

In the case of the polyether glycols used and in the case of the polyether glycol esters (JP-A 55-120 581), there is another significant disadvantage in that they have functional groups which participate in the polymerization in an undesired manner, possibly leading to significant yield losses. In addition, in the case of the paraffins, the difficulty also arises that they have relatively high vapor pressures compared with the reactants and therefore also convert to the vapor phase. For this reason, in the case of these paraffins, isolation of the product, which follows the depolymerization of the oligoester, is associated with significantly higher expenditure.

Moreover, high-boiling reaction media such as, for example paraffins (DE-A 32 25 341) or olefin polymers (EP-A 0 260 680) are less suitable solvents for all linear poly- or oligoesters. In many cases they only disperse said esters, and the particles may coagulate to form blocks. A remedy is achieved in most cases by further dilution, as a result of which the space-time yield is significantly reduced, as is the case with known processes.

In addition, JP-B 55-120581 describes a process for carrying out the depolymerization and cyclization in the presence of polyoxyalkylene glycol and derivatives thereof, monohydric alcohols and derivatives thereof or monobasic fatty acids and derivatives thereof which in each case have a high boiling point. According to this process, ether bonds in the polyoxyalkylene glycol added are broken and, as a result, various degradation products or gases are formed and, consequently, the vacuum is lower or the quality of the resulting macrocyclic ester compound is impaired. In addition, the odor of the monohydric alcohol or of the monobasic acid or of derivatives thereof mix with the distillate and as a result the scent of the macrocyclic ester compound is impaired and its use as a perfume is impeded. These phenomena are regarded as disadvantages of these customary processes.

Finally, the use of polyethylene glycol dialkyl ethers (EP A 0 739 889) is associated with the disadvantage that the desired effect of an increase in the yield is achieved only at sufficiently great dilution ratios; for example, in EP A 0 739 889, dilution ratios between 5 and 1000 parts by weight of polyethylene glycol dialkyl ether to 1 part by weight of oligomer are given. A further important disadvantage of the use of polyethylene glycol dialkyl ethers is also that a work-up of the solvent is not readily possible and therefore, by-products which contaminate the solvent considerably limit the suitability of the solvent.

SUMMARY OF THE INVENTION

The object of the present invention was, therefore, to find a preparation process for macrocyclic ester compounds with which as high a reaction yield as possible can be achieved and with which, the solvent costs can also be reduced, by using a solvent which restricts the formation of by-products which prevent use of the macrocyclic ester compounds as a fragrance, which has a low melting point and thus, good handling properties, which simplifies product separation by virtue of having a high boiling point, and which can be worked-up readily for reuse in the process without relatively large losses as a result of residue formation.

We have now found a process for the preparation of macrocyclic ester compounds obtainable from linear oligoesters by thermal depolymerization with or without the addition of catalysts, which is characterized in that the depolymerization is carried out in thermostable benzene derivatives at a pressure of less than 100 hPa, and at temperatures of from 200° C. to 350° C., 0.1 to 1000 parts by weight of solvent being used per part by weight of the oligoester.

DETAILED DESCRIPTION OF THE INVENTION

Macrocyclic ester compounds which can be prepared by the process according to the present invention are generally 14- to 17-member ring systems. They can be described by the following general formula

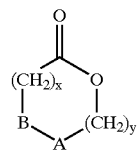

in which x and y produce in total a number of at least 10 and at most 13;

A may be a methylene group or a heteroatom, such as oxygen or sulfur;

B may be a methylene group or a carbonyl group or

A and B taken together may be a carbon double-bond.

Preferably, the process according to the present invention may be used to prepare macrocyclic lactones of ω-hydroxycarboxylic acids which may optionally comprise a double bond and/or a further heteroatom, e.g. oxygen, or macrocyclic lactones of dicarboxylic acids and diols.

Particularly preferably, the process according to the present invention can be used to prepare 1,15-pentadecanolide, cis-/trans-1,15-pentadec-11-enolide, cis-/trans-1,15-pentadec-12-enolide or mixtures thereof, 1,16-hexadecanolide or trans-1,16-hexadec-9-enolide or ethylene tridecadioate, ethylene dodecadioate or ethylene undecadioate or mixtures thereof.

The linear oligoesters for the process according to the present invention can be described by the following general formula:

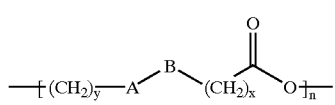

in which x and y produce in total a number of at least 10 and at most 13;

A may be a methylene group or a heteroatom, such as oxygen or sulfur;

B may be a methylene group or a carbonyl group or

A and B taken together may be a carbon double-bond.

For the process according to the present invention, oligoesters of aliphatic hydroxycarboxylic acids or oligoesters of dicarboxylic acids with diols are preferred.

Linear oligoesters as starting compounds for the process according to the present invention can be prepared by condensation of difunctional compounds of the formula

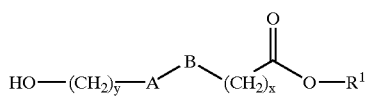

in which x and y produce in total a number of at least 10 and at most 13;

A may be a methylene group or a heteroatom, such as oxygen or sulfur;

B may be a methylene group or A and B taken together may be a carbon double-bond;

$R^1$ may be a hydrogen atom or a lower alkyl group, such as, for example, methyl or ethyl, or of the formula

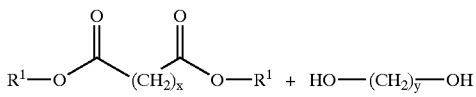

in which x and y produce in total a number of at least 10 and at most 13;

$R^1$ may be a hydrogen atom or a lower alkyl group, such as, for example, methyl or ethyl, in a manner known per se (DE B 2731543; Houben-Weyl, Methoden der Organischen Chemie [Methods of Organic Chemistry] Vol. 4/2, p. 787ff. and Vol. 6/2, p. 738f.).

The process according to the present invention is based on a thermal cleavage of oligoesters to the desired macrocyclic esters. The cleavage reaction is carried out in a vacuum and at very high temperatures in an inert, high-boiling reaction medium with or without the addition of catalysts, a rectification column being placed on top of the container in which the chemical reaction takes place and used to separate off and concentrate the macrocyclic esters formed. Here, the thermal cleavage is carried out in thermostable, high-boiling alkylbenzene or benzene derivatives, e.g. of the formula

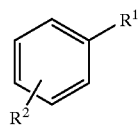

in which
R$^1$ is

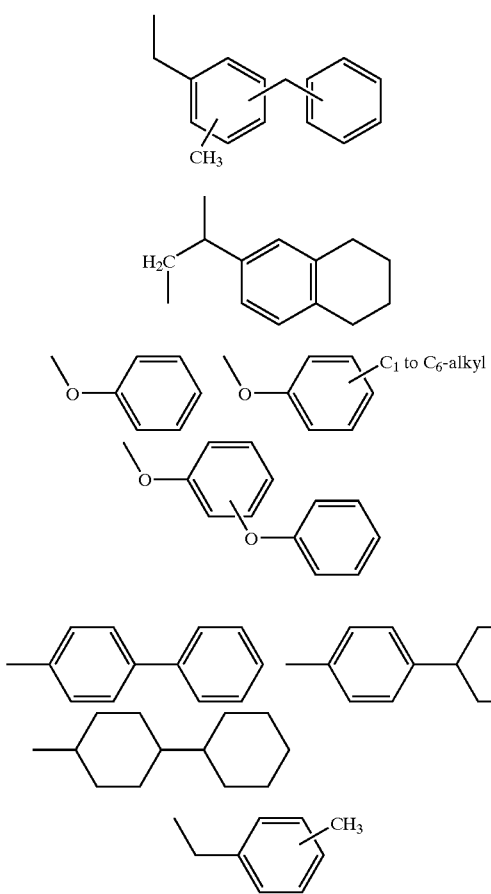

and
R$^2$ is H or CH$_3$ as reaction medium. By using these thermostable benzene derivatives, the yield is significantly increased compared with a cleavage without a diluent. The derivatives of type a) are essentially isomeric dibenzyltoluenes, b) refers to the group of diarylalkyls, c) represents the bi- or triaryl oxides, d) includes the group of terphenyls and their partially hydrogenated analogues and, finally, e) represents the alkylated or non-alkyl-substituted benzyltoluenes.

Preferred thermostable benzene derivatives are dibenzyltoluenes and isomer mixtures thereof, and terphenyls and their partially hydrogenated analogues. A more preferred embodiment is dibenzyltoluenes and isomeric mixtures thereof.

The thermostable benzene derivatives for the process according to the present invention have a low melting point and a high boiling point at the same time. However, despite the high boiling point, they are very vaporizable and can, therefore, be separated readily from high-boiling impurities. Their use as reaction medium is therefore advantageous both with regard to handling and also with regard to product separation. For example separation of the product from the reaction medium is possible in a rectification column with only a few separation stages, the number of separation stages required and the reflux ratio to be set being governed by the difference in boiling points between the macrocyclic ester formed and the solvent used.

If benzene derivatives are used, reaction yields of more than 90% can be achieved. In this connection, it is essential for the economic efficiency of the process that the high reaction yields can be achieved at low solvent costs. This is possible, in particular, by setting low dilution ratios of solvent to oligomer during the depolymerization and, moreover, working-up the spent solvent for recycle and reuse in the process.

It was surprising that the benzene derivatives used as reaction medium for the thermal depolymerization are stable. This was unexpected since alkyl- and benzyl-substituted benzene derivatives in the presence of the catalysts suitable for the depolymerization and at the high reaction temperatures are able to undergo transalkylation reactions, in the course of which high-boiling and low-boiling components are formed as a result of disproportionation. As well as a solvent loss, this would also permanently impair the suitability of the solvent since low-boiling solvent constituents accumulate in the product, and the high-boiling constituents can lead to resinification of the distillation bottoms.

In particular, dibenzene toluene, which is available in technical-grade form as an isomer mixture, has an excellent profile of properties for the process according to the present invention, since it permits particularly effective separation from the product which distills off, as a result of its high, comparatively narrow boiling range.

For reasons of simplicity, the condensation of the difunctional compounds to give the linear oligoesters is connected upstream of the process according to the present invention.

Implementation of the process is, therefore, first started with the condensation, which can be carried out in accordance with known methods at elevated temperatures with or without catalyst. In this process, hydroxycarboxylic acids, or hydroxycarboxylic esters are heated, or the dicarboxylic acids or esters thereof are reacted with a glycol. The water which forms in the process or the alcohol is distilled off or removed using an entrainer or with the help of a slight vacuum. The removal of some or all of the excess glycol can also be carried out in the subsequent process step, i.e. from the cleavage reactor.

The oligomer is then transferred to the cleavage reactor, into which the high-boiling medium has been introduced together with the catalyst component. The catalysts used are customary catalysts known per se (EP A 0 739 889), such as, for example, alkali metals and alkaline earth metals and salts thereof, and salts and organometallic compounds of the elements manganese, cadmium, iron, cobalt, tin, lead, aluminium, zirconium and titanium. The amount of catalyst is in the range from 0.1 to 20% by weight, preferably in the range from 0.5 to 10% by weight, based on 100% by weight of oligoester, depending on the corresponding type used.

At high temperatures between 200° C. and 350°C., preferably between 220° C. and 290° C., and at a vacuum of less than 100 hPa, the depolymerization then takes place. The cleavage products preferably rise during the process in the form of vapors and are thus, withdrawn directly from the reaction in the liquid phase. The product components can be separated from the components of the reaction medium in a rectification column placed on top of the reaction container, at the upper end of the column the product components being withdrawn, and at the lower end of the column the components of the reaction mixture being taken off for recycling to the reaction container. The column is operated for this purpose at pressures of <100 hPa, the pressure range preferably being from 5 to 95 hPa, particularly preferably from 10 to 80 hPa. At the top of the column, a reflux ratio between 0.1 and 100, preferably between 10 and 80, is to be set.

The process can either be carried out either batchwise or continuously. In the case of a batchwise procedure, the oligomer is introduced in one portion together with the solvent and cleaved in one batch. By contrast, in the case of the continuous procedure, the oligomer is metered into the reaction medium during the cleavage in portions or with a constant material stream. Preference is given to carrying out the continuous procedure since in this case the product can be removed from the top of the column with a constant composition.

The solvent is recovered by partial evaporation, for example in a thin-layer evaporator at pressures of less than 100 hPa, preferably at pressures of less than 50 hPa.

A very wide variety of macrocyclic ester compounds can be prepared by this process. It is particularly suitable for the preparation of macrocyclic esters having 6 to 20, preferably 13 to 16, carbon atoms, since they can be prepared in particularly pure form by the process according to the present invention, which is highly beneficial to their use as fragrances. In particular, using the process according to the present invention, it is also possible to prepare the mixtures of ethylene dodecanedioate and ethylene undecanedioate described in U.S. Pat. No. 6,034,052.

EXAMPLES

Example 1

Preparation of Ethylene Tridecanedioate a) Preparation of Ethylene Glycol Tridecanedioic Polyester 500 g of a dimethyl tridecanedioate, 250 g of ethylene glycol and 3 g of tetrabutyl titanate are heated slowly under a vacuum of 300 hPa in a reaction distillation apparatus. As soon as a reaction temperature of 140° C. has been reached, methanol starts to be eliminated. The heating is continued until methanol is no longer eliminated; in this connection, the still temperature is slowly increased to 185° C. The vacuum is let down to 1 hPa, and the excess ethylene glycol is distilled off. 510 g of polyester are obtained as residue.

b) Depolymerization of the Ethylene Glycol Tridecanedioc Polyester

A molten mixture comprising 2 parts by weight of dibenzyltoluene (isomer mixture), 1 part by weight of ethylene glycol tridecanedioic polyester and 0.02 parts by weight of dibutyltin dilaurate is metered into a reaction container with attached rectification column, which contains a mixture of 2 parts by weight of dibenzyltoluene (isomer mixture) and 0.02 parts by weight of dibutyltin dilaurate, which is heated to about 280° C. and refluxed at a pressure of 55 hPa. The formation of monomeric ethylene tridecanedioate becomes evident from a reduction in the temperature at the distillation head. The distillate is removed at the rate which polyester is replenished. Depending on the separation efficiency of the attached rectification column and the chosen reflux ratio, the distillate removed comprises between 30 and 98% ethylene tridecanedioate, which is obtained in pure form in a subsequent fine distillation. By this method, the yield is about 90%, based on the dimethyl tridecanedioate used.

By distilling the reaction residue, more than 90% of the dibenzyltoluene used are recovered.

Example 2

Preparation of a Mixture of Ethylene Dodecanedioate and Ethylene Undecanedioate a) Preparation of the Polyester 225 g of a technical-grade mixture comprising between 40 and 60% of dodecanedioic acid and 30–50% of undecanedioic acid are admixed with 105 g of ethylene glycol and slowly heated to 150°C.; at about 130° C. to 140° C., water starts to be eliminated. When water elimination is complete, to remove excess ethylene glycol, the temperature is increased to 170° C. and the reaction apparatus is slowly evacuated to a pressure of 1 hPa.

b) Depolymerization

The dicarboxylic acid/ethylene glycol polyester resulting as residue is admixed, per part by weight of polyester, with 3 parts by weight of dibenzyltoluene (isomer mixture) and 0.05 parts by weight of dibutyltin dilaurate and heated in a reaction container with attached rectification column at a pressure of 55 hPa at about 280° C. and refluxed. In the process, the monomeric cleavage products distil over. At the start, the distillate comprises, depending on the composition of the starting material, between 40–60% of ethylene dodecanedioate and 30 to 50% of ethylene undecanedioate, and in the further course of the reaction, increasingly also small amounts of dibenzyltoluenes, which are separated off in a subsequent fine distillation. Overall, a reaction yield of about 91% is achieved in the depolymerization. By distilling the reaction residue, more than 90% of the dibenzyltoluene used are recovered.

Example 3

Preparation of a Mixture of Ethylene Dodecanedioate and Ethylene Undecanedioate a) Polymerization 250 g of ethylene glycol, 500 g of a technical-grade mixture consisting of 40 to 60% of dimethyl dodecanedioate and 30–50% of dimethyl dodecanedioate, and 3 g of tetrabutyl titanate are heated slowly under a vacuum of 300 hPa in a reaction distillation apparatus. At a reaction temperature of between 130–140° C., methanol starts to be eliminated, which is distilled off over a 30 cm packed column. Heating is continued until methanol is no longer eliminated; here, the still temperature is slowly increased to 185° C. The vacuum is then let down to 1 hPa, and the excess ethylene glycol is distilled off. 500 g polyester are obtained as residue.

b) Depolymerization

A molten mixture comprising 500 g of dibenzyltoluene (isomer mixture), 250 g of the diacid ethylene glycol polyester mixture obtained as in a) and 5 g of dibutyltin dilaurate is metered into a reaction container with attached rectification column which contains a mixture of 500 g of dibenzyltoluene (isomer mixture) and 5 g of dibutyltin dilaurate, which is heated to about 280° C. and is refluxed at a pressure of 55 hPa. The formation of monomeric esters becomes evident from a reduction in the temperature at the distillation head. As soon as the head temperature has dropped below 220° C., the distillate is taken off and polyester mixture is continuously replenished. Depending on the separation efficiency of the attached rectification column and the chosen reflux ratio, the distillate taken off comprises between 30 and 98% of a mixture of the monomers ethylene dodecanedioate and ethylene undecanedioate. In the present case, at a head temperature of 220–225° C. and a reflux ratio of 15:1 490 g of distillate with a weight fraction of 225 g of ethylene dodecanedioate and ethylene undecanedioate mixture were obtained, which corresponds to a yield of 90%, based on dicarboxylic acid dimethyl ester mixture used. The mixture of ethylene dodecanedioate and ethylene undecanedioate was separated off from the dibenzyltoluene in a subsequent fine distillation and thus obtained in pure form. By distilling the reaction residue, more than 90% of the dibenzyltoluene used are recovered.

Example 4

Preparation of 1,15-Pentadecanolide a) Preparation of the Polyester 260 g of 15-hydroxypentadecanoic acid are slowly heated to 170° C. under a slight vacuum (650 hPa). As soon as the elimination of water has subsided, the mixture is stirred for a further 1 h at a vacuum of 20 hPa and for 30 min at a vacuum of 1 hPa. The polyester of 15-hydroxypentadecanoic acid is left behind as residue.

b) Depolymerization

A molten mixture comprising 1 part by weight of the 15-hydroxy-pentadecanoic polyester left behind as residue, 2 parts by weight of dibenzyltoluene (isomer mixture) and 0.02 parts by weight of dibutyltin dilaurate is metered into a reaction container with attached rectification column which contains a mixture of 2 parts by weight of dibenzoyltoluene (isomer mixture) and 0.02 parts by weight of dibutyltin dilaurate, which is heated to about 280° C. and is refluxed at a pressure of 55 hPa. The formation of monomeric 1,15-pentadecanolide becomes evident from a reduction in the temperature at the distillation head. Distillate is taken off at the rate at which polyester is replenished. Depending on the separation efficiency of the attached rectification column and the reflux ratio chosen, the distillate taken off comprises between 30 and 95% of 1,15-pentadecanolide. In the present case, at a head temperature of 215–220° C. and a reflux ratio of 10:1, a distillate with a weight fraction of about 60% of 1,15-pentadecanolide was obtained, which is obtained in pure form in a subsequent fine distillation. The yield of the 1,15-pentadecanolide obtained in this way is 85%, based on 15-hydroxypentadecanoic polyester used. By distilling the reaction residue, more than 90% of the dibenzyltoluene used are recovered.

Example 5

Preparation of cis-/trans-1, 15-Pentadec-11/12-enolide a) Preparation of the polyester 260 g of cis-/trans-15-hydroxy-11/12-pentadecenoic acid are slowly heated to 170° C. under a slight vacuum (650 hPa). As soon as the elimination of water subsides, the mixture is stirred for a further 1 h at a vacuum of 20 hPa and for 30 min at a vacuum of 1 hPa. The polyester of 15-hydroxypent-adecanoic acid is left behind as residue.

b) Depolymerization

A molten mixture comprising 1 part by weight of the cis-/trans-15-hydroxy-11/12-pentadecanoic polyester which is left behind as residue, 2 parts by weight of dibenzyltoluene (isomer mixture) and 0.02 parts by weight of dibutyltin dilaurate is metered into a reaction container with attached rectification column which contains a mixture of 2 parts by weight of dibenzyltoluene (isomer mixture) and 0.02 parts by weight of dibutyltin dilaurate, which is heated to about 280° C. and refluxed at a pressure of 55 hPa. The formation of monomeric cis-/trans-1, 15-pentadec-11/12-enolide is evident from a reduction in temperature at the distillation head. The distillate is taken off at the rate at which the polyester is replenished. According to the separation efficiency of the attached rectification column and the reflux ratio chosen, the distillate taken off comprises between 30 and 90% of 1,15-pentadecanolide. In the present case, at a head temperature of 210–215° C. and a reflux ratio of 10:1, a distillate with a weight fraction of about 60% cis-/trans-1,15-pentadec-11/12-enolide is obtained, which is obtained in pure form in a subsequent fine distillation.

The yield of cis-/trans-1,15-pentadec-11/12-enolide obtained in this way is about 85%, based on 15-hydroxypenta-decanoic polyester used.

By distilling the reaction residue, more than 90% of the dibenzyltoluene used are recovered.

Example 6

Preparation of 1,16-Hexadecanolide a) Preparation of the polyester 140 g of 16-Hydroxyhexadecanoic acid are slowly heated to 170° C. under a slight vacuum (650 hPa). As soon as the elimination of water subsides, the mixture is stirred for a further 1 h at a vacuum of 20 hPa and for 30 min at a vacuum of 1 hPa. The polyester of 16-hydroxyhexadecanoic acid is left behind as residue.

b) Depolymerization

A molten mixture of 1 part by weight of the 16-hydroxyhexadecanoic polyester which is left behind as residue, 2 parts by weight of dibenzyltoluene (isomer mixture) and 0.02 parts by weight of dibutyltin dilaurate is metered into a reaction container with attached rectification column which contains a mixture of 2 parts by weight of dibenzyltoluene (isomer mixture) and 0.02 parts by weight of dioctyltin dilaurate, which is heated to about 280° C. and refluxed at a pressure of 55 hPa. The formation of monomeric 1,16-hexadecanolide is evident from a reduction in the temperature at the distillation head. Distillate is taken off at the rate at which polyester is replenished. Depending on the separation efficiency of the attached rectification column and the reflux ratio chosen, the distillate taken of comprises between 30 and 90% of 1,16-hexadecanolide. In the present case, at a head temperature of 220–230° C. and a reflux ratio of 5:1, a distillate with a weight fraction of about 50% of 1,16-hexadecanolide is obtained, which is obtained in pure form by subsequent fine distillation. The yield of 1,16-hexadecanolide achieved in this way is about 75%, based on 16-hydroxyhexadecanoic polyester used. By distilling the reaction residue, more than 90% of the dibenzyltoluene used are recovered.

Example 7

Preparation of trans-1,16-Hexadec-9-enolide a) Preparation of the polyester 260 g of trans-16-hydroxy-9-hexadecenoic acid are slowly heated to 170° C. under a slight vacuum (650 hPa). As soon as the elimination of water has subsided, the mixture is stirred for a further 1 h at a vacuum of 20 hPa and for 30 min at a vacuum of 1 hPa. The polyester of trans-16-hydroxy-9-hexadecanoic acid is left behind as residue.

b) Depolymerization

A molten mixture comprising 1 part by weight of the trans-16-hydroxy-9-hexadecenoic polyester which is left behind as residue, 2 parts by weight of dibenzyltoluene (isomer mixture) and 0.02 parts by weight of dibutyltin dilaurate is metered in to a reaction container with attached rectification column which contains a mixture of 2 parts by weight of dibenzyltoluene (isomer mixture) and 0.02 parts by weight of dibutyltin dilaurate, which is heated to about 280° C. and refluxed at a pressure of 55 hPa. The formation of monomeric trans-, 16-hexadec-9-enolide is evident from a reduction in the temperature at the distillation head. Distillate is taken off at the rate at which polyester is replenished. Depending on the separation efficiency of the attached rectification column and the chosen reflux ratio, the distillate taken off comprises between 30 and 90% of trans-1,16-hexadec-9-enolide.

In the present case, at a head temperature of 225–235° C. and a reflux ratio of 10:1, a distillate with a weight fraction of about 60% of trans-1,16-hexadec-9-enolide was obtained, which is obtained in pure form in a subsequent fine distillation. The yield of trans-1,16-hexadec-9-enolide achieved in this way is about 80%, based on trans-16-hydroxy-9-hexadecenoic polyester used. By distilling the reaction residue, more than 90% of the dibenzyltoluene used are recovered.

Example 8

Preparation of a Mixture of Ethylene Dodecanedioate and Ethylene Undecanedioate

A molten mixture of 260 g of partially hydrogenated terphenyl (isomer mixture, trade name Diphyl THT, Bayer AG), 130 g of the diacid ethylene glycol polyester mixture obtained as in Example 3a), and 6.4 g of dibutyltin dilaurate is metered into a reaction container with attached rectification column which contains a mixture of 500 g of partially hydrogenated terphenyl (isomer mixture, see above), which is heated to about 280° C. and refluxed at a pressure of 110 hPa. The formation of monomeric esters is evident from a reduction in the temperature at the distillation head. As soon as the head temperature has dropped below 240° C., distillate is taken off and polyester mixture is continuously replenished. Depending on the separation efficiency of the attached rectification column and the reflux ratio chosen, the distillate taken off comprises between 20 and 90% of a mixture of the monomers ethylene dodecanedioate and ethylene undecanedioate. In the present case, at a head temperature of 238–240° C. and a reflux ratio of 10:1, 250 g of distillate with a weight fraction 95 g of ethylene dodecanedioate and ethylene undecanedioate mixture were obtained, which corresponds to a yield of 70%, based on dicarboxylic dimethyl ester mixture used. The mixture of ethylene dodecanedioate and ethylene undecanedioate was separated off from the partially hydrogenated terphenyl in a subsequent fine distillation and thus obtained in pure form.

By distilling the reaction residue, more than 90% of the partially hydrogenated terphenyl used are recovered.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of macrocyclic ester compounds comprising the steps of condensating difunctional compounds to give linear oligoesters and subsequently, thermal depolymerization with or without the addition of catalysts, wherein the depolymerization is carried out in thermostable benzene derivatives at a pressure of less than 100 hPa and at temperatures of from 200° C. to 350° C., 0.1 to 1000 parts by weight of solvent being used per part by weight of the oligoester.

2. The process according to claim 1, wherein thermostable benzene derivatives of the formula

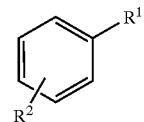

in which
R$^1$ is

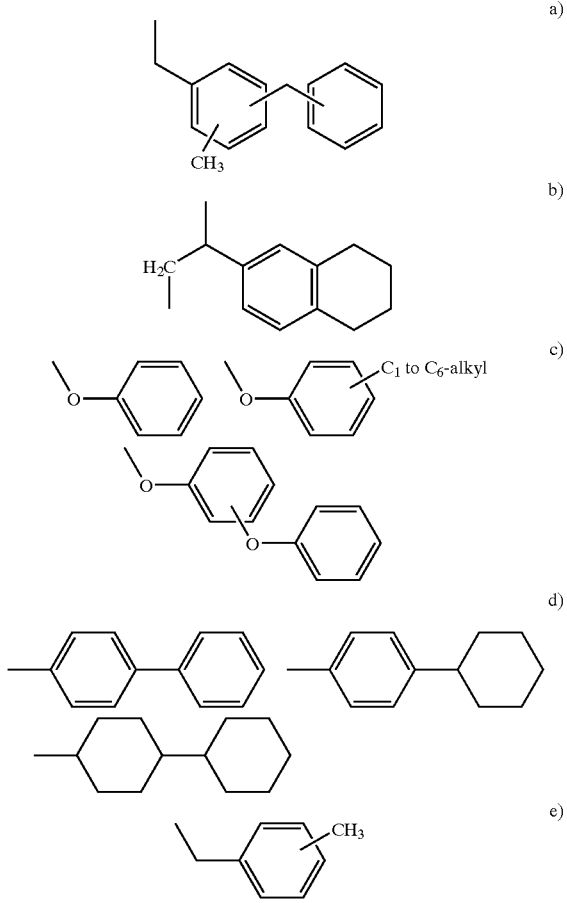

and
R$^2$ is H or CH$_3$,
are used.

3. The process according to claim 2, wherein isomeric dibenzyltoluenes are used as thermostable benzene derivatives.

4. The process according to claim 1, wherein said catalysts are the alkali metals or alkaline earth metals or salts thereof, or salts or organometallic compounds of the elements manganese, cadmium, iron, cobalt, tin, lead, aluminium, zirconium or titanium.

5. The process according to claim 4, where dibutyltin oxide, dioctyltin oxide, dibutyltin dilaurate, dioctyltin dilaurate, dibutyltin bis-2-ethylhexanoate, butyltin tris-2-ethylhexanoate, butyltin hydroxide oxide or cyclic dibutyl stannoxane are used as catalyst.

6. The process according to claim 1, wherein the catalyst is replenished in portions or continuously in order to achieve constant concentrations of the active form of the catalyst.

7. The process according to claim 1, wherein a rectification column, from the top of which the macrocyclic ester formed is removed, is placed on top of the reaction container.

8. The process according to claim 1, wherein the thermostable benzene compound is freed from high-boiling reaction residues in an amount of more than 50 percent by weight by partial evaporation, and is then reused as reaction medium in the oligoester depolymerization.

* * * * *